US006812360B2

United States Patent
Ikeno et al.

(10) Patent No.: US 6,812,360 B2
(45) Date of Patent: Nov. 2, 2004

(54) PROCESS FOR PREPARING BIS(FLUOROARYL)BORON DERIVATIVES

(75) Inventors: Ikuyo Ikeno, Osaka (JP); Hitoshi Mitsui, Kitakatsuragi-gun (JP); Toshiya Iida, Suita (JP); Toshimitsu Moriguchi, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/221,029
(22) PCT Filed: Nov. 28, 2001
(86) PCT No.: PCT/JP01/10392
§ 371 (c)(1), (2), (4) Date: Sep. 9, 2002
(87) PCT Pub. No.: WO02/44185
PCT Pub. Date: Jun. 6, 2002

(65) Prior Publication Data
US 2003/0045507 A1 Mar. 6, 2003

(30) Foreign Application Priority Data
Nov. 30, 2000 (JP) .................................... 2000-369621

(51) Int. Cl.$^7$ ................................................ C07F 5/02
(52) U.S. Cl. ................................ 556/7; 568/1; 568/6
(58) Field of Search ........................... 568/1, 6; 556/7; 562/7; 558/286, 298

(56) References Cited

U.S. PATENT DOCUMENTS 2,862,952 A * 12/1958 Groszos ..................... 558/298

FOREIGN PATENT DOCUMENTS

WO 00/37476 A1 6/2000

OTHER PUBLICATIONS

CA:135:211145 abs of DE 10059717 Sep. 2001.*

CA:63:89010 abs of Chemische Berichte by Niedenzu et al 98(8) pp 3050–2 1965.*

"Polyfluoraoryl Organometallic Compounds. Part II. Pentafluorophenylboron Halides and Some Derived Compounds" (R.D. Chambers et al., J.Chem.Soc.(1965) pp 3933–3939).

"Borane–functionalized Oxide Supports: Development of Active Supported Metallocene Catalysts at Low Aluminoxane Loading" (Jun Tian et al., Journal of Molecular Catalysis A: Chemical 144 (1999) pp 137–150).

* cited by examiner

Primary Examiner—Brian Davis
(74) Attorney, Agent, or Firm—Nixon & Vanderhye P.C.

(57) ABSTRACT

Bis(fluoroaryl)borane derivative is produced by reacting tris(fluoroaryl)borane with a compound, such as water, ethanol, ammonia and the like, in a hydrocarbon solvent at a molar ratio raging from 1:0.9 to 1:1.1. It is more preferable that the reaction is carried out while the hydrocarbon solvent is distilled off. It is more preferable that hydrocarbon solvent is substantially an aliphatic hydrocarbon solvent. With this arrangement, it is possible to provide a method for producing and isolating the bis(fluoroaryl)borane derivative of a high purity, with ease and at a low cost.

9 Claims, No Drawings

PROCESS FOR PREPARING BIS(FLUOROARYL)BORON DERIVATIVES

This application is a 371 of PCT/JP01/10392 filed Nov. 28, 2001.

TECHNICAL FIELD

The present invention relates to a method for producing a bis(fluoroaryl)borane derivative such as a bis(pentafluorophenyl)borinic acid, which is useful as a polymerization catalyst, a polymerization co-catalyst, a catalyst for photopolymerization of silicone, an intermediate thereof, and an intermediate of a medicine or an agricultural chemical, for example.

BACKGROUND ART

Bis(fluoroaryl)borane derivatives such as bis(pentafluorophenyl)borinic acid, are compounds useful as polymerization catalysts, polymerization co-catalysts, catalysts for photopolymerization of silicone, intermediates thereof, and intermediates of medicines or agricultural chemicals, for example.

For instance, as a manufacturing method of bis(pentafluorophenyl)borinic acid, J. Chem. Soc (1965) 3933–3939 discloses a method in which water is added to bis(pentafluorophenyl) chloro borane in acetone at a temperature of −20° C., then the acetone solution is concentrated, so that the bis(pentafluorophenyl)borinic acid is sublimated for purification, so as to be isolated. Furthermore, bis(pentafluorophenyl) chloro borane, which is a precursor of bis(pentafluorophenyl)borinic acid, is synthesized by reacting bis(pentafluorophenyl) dimethyl tin with boron trichloride. However, it is difficult to purify bis(pentafluorophenyl) chloro borane, because dimethyltin dichloride, which is a byproduct of the reaction, is sublimated when bis(pentafluorophenyl) chloro borane is isolated by distillation.

Moreover, J. Molecular Catalysis A: Chemical 144 (1999) 137–150 and WO 0037376 (2000) disclose that bis(pentafluorophenyl)borinic acid is prepared by heating tris(pentafluorophenyl)borane hydrate.

However, the method disclosed in the above-mentioned J. Molecular Catalysis A: Chemical 144 (1999) 137–150 discloses only how to manufacture bis(pentafluorophenyl)borinic acid, and fails to recite how to isolate bis(pentafluorophenyl)borinic acid from a reaction mixture, even though easy isolation and purification of the bis(fluoroaryl)borane derivative are necessary for industrial application of the bis(fluoroaryl)borane derivative as a catalyst or the like.

J. Molecular Catalysis A: Chemical 144 (1999) 137–150 recites only that it was confirmed by $^{19}$F-NMR that bis(pentafluorophenyl)borinic acid was prepared by adding water to a toluene-d8 solution of tris(pentafluorophenyl) borane so as to prepare tris(pentafluorophenyl)borane hydrate, then heating the solution of tris(pentafluorophenyl) borane hydrate.

Moreover, WO 0037476 (2000) discloses preparation of bis(pentafluorophenyl)borinic acid by heating tris(pentafluorophenyl)borane hydrate, and an isolation method of bis(pentafluorophenyl)borinic acid. Specifically, a toluene solution of tris(pentafluorophenyl)borane is heated up to 100° C. Then, to the solution, a toluene solution containing water of 2.5 molar equivalent is dropped so that reaction is carried out at 100° C. After the reaction, the solvent is concentrated in vacuo to dryness so as to isolate bis(pentafluorophenyl)borinic acid. However, it is recited that the bis(pentafluorophenyl)borinic acid obtained by this method contained boroxine by 5% as impurities. In short, this method has such a problem that the isolated bis(pentafluorophenyl)borinic acid has a low purity.

Moreover, that patent also discloses a method in which aluminum sulfate 18 hydrate is used instead of water. Specifically, aluminum sulfate 18 hydrate containing water of 1.77 molar equivalent vs. tris(pentafluorophenyl)borane is added to a toluene solution of tris(pentafluorophenyl) borane. After the solution is refluxed, insoluble aluminum sulfate is separated from the reaction mixture. A solvent of the filtrate is removed in vacuo. Toluene is added to the thus obtained residues. After stirring, the insoluble material is filtered through a G4 sintered-glass so as to be separated. The solvent of the filtrate is again removed in vacuo. Heptane is added to the residues. The solution is stirred and filtered so that a cake is obtained. Finally, the thus obtained cake is washed with heptane, and dried in vacuo so as to isolate bis(pentafluorophenyl)borinic acid. However, this method has such a problem that it is necessary to remove the byproduct aluminum sulfate and its process is so complicated.

Therefore, for industrial application of a bis(fluoroaryl) borane derivative, such as bis(pentafluorophenyl)borinic acid, as a catalyst or the like, there is a desire for a method by which the bis (fluoroaryl)borane derivative is easily isolated from a reaction mixture, and purified. Thus, the present invention, which is contrived in view of the foregoing problems, has an object of providing a method by which a bis(fluoroaryl)borane derivative can be produced, isolated, and purified with ease and at a low cost.

For a fuller understanding of the nature and advantages of the invention, reference should be made to the ensuing detailed description taken in conjunction with the accompanying drawings.

DISCLOSURE OF INVENTION

The inventor of the present invention, in order to attain the above-mentioned object, carried out an intensive study on a method for producing a bis(fluoroaryl)borane derivative such as bis(pentafluorophenyl)borinic acid. As a result, a molar ratio between tris(fluoroaryl)borane and a compound was studied, the tris(fluoroaryl)borane being represented by General Formula (1):

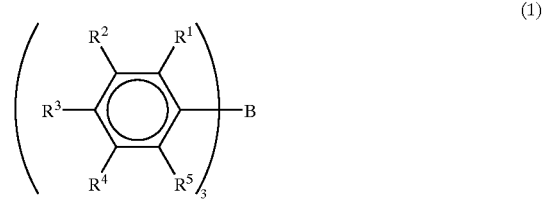

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom), the compound being represented by General Formula (2):

$$R^0\text{—}MR^6(R^7)_n \qquad (2)$$

(where each of $R^0$, $R^6$, and $R^7$ independently represents one of a hydrogen atom and a hydrocarbon group, M represents an atom belonging to Group 15 or Group 16, and n represents 0 or 1). As a result, it was found that reaction rate was extremely decreased as the molar ratio was increased. Further, it was found that selectivity coefficient of the bis(fluoroaryl)borane derivative, which is a target compound, is decreased as the molar ratio is increased, the bis(fluoroaryl)borane derivative being represented by General Formula (3):

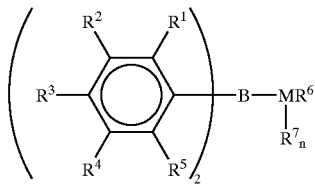
(3)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, R3, $R^4$, and $R^5$ representing the fluorine atom, and each of $R^6$ and $R^7$ independently represents one of a hydrogen atom and a hydrocarbon group, M represents an atom belonging to Group 15 or Group 16, and n represents 0 or 1), so that an optimal molar ratio between General Formulas (1) and (2) was found. Specifically, it was found that a bis (fluoroaryl)borane derivative having a high purity can be easily produced by having a molar ratio of 1:0.9 to 1:1.1 between the General Formulas (1) and (2). It was found that a hydrocarbon solvent is preferable as a reaction solvent, and that the bis(fluoroaryl) borane derivative can be isolated by concentrating a reaction mixture obtained by the reaction, more preferably by filtering the thus concentrated reaction mixture.

Specifically, in order to attain the above-mentioned object, a method of the present invention for producing a bis(fluoroaryl)borane derivative represented by General Formula (3):

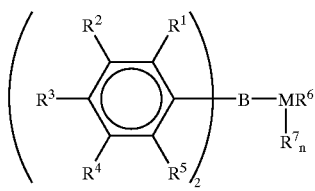
(3)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom, and each of $R^6$ and $R^7$ independently represents one of a hydrogen atom and a hydrocarbon group, M represents an atom belonging to Group 15 or Group 16, and n represents 0 or 1), includes the step of reacting tris (fluoroaryl)borane and a compound in a hydrocarbon solvent, in a molar ratio ranging from 1:0.9 to 1:1.1, the tris(fluoroaryl)borane being represented by General Formula (1):

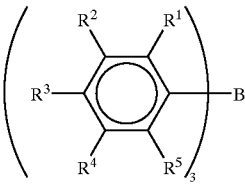
(1)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom), the compound being represented by General Formula (2):

$R^0$—$MR^6(R^7)_n$ (2)

(where each of $R^0$, $R^6$, and $R^7$ independently represents one of a hydrogen atom and a hydrocarbon group, M represents an atom belonging to Group 15 or Group 16, and n represents 0 or 1).

In order to attain the above-mentioned object, a method of the present invention for producing a bis(fluoroaryl)borane derivative represented by General Formula (3):

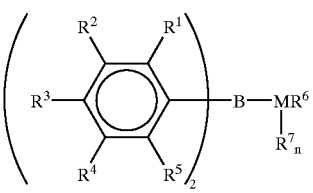
(3)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom, and each of $R^6$ and $R^7$ independently represents one of a hydrogen atom and a hydrocarbon group, M represents an atom belonging to Group 5B or Group 6B, and n represents 0 or 1), includes the steps of mixing tris (fluoroaryl)borane and a compound in a hydrocarbon solvent, in a molar ratio ranging from 1:0.9 to 1:1.1, and reacting the tris(fluoroaryl) borane and the compound in a hydrocarbon solvent, while the hydrocarbon solvent is distilled off, the tris(fluoroaryl) borane being represented by General Formula (1):

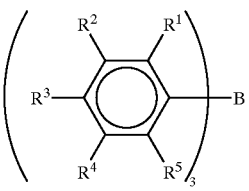
(1)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom), the compound being represented by General Formula (2):

$R^0$—$MR^6(R^7)_n$ (2)

(where each of $R^0$, $R^6$, and $R^7$ independently represents one of a hydrogen atom and a hydrocarbon group, M represents an atom belonging to Group 15 or Group 16, and n represents 0 or 1).

The method of the present invention for producing the bis(fluoroaryl)borane derivative includes reacting the tris(fluoroaryl)borane and the compound (hereinafter, just referred to as the "compound (2)") represented by General Formula (2) in the hydrocarbon solvent.

The tris(fluoroaryl)borane used as a starting raw material in the present invention is a compound represented by General Formula (1):

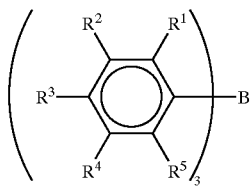
(1)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom).

In the general formula, specifically, the hydrocarbon group for the substitutional groups represented by $R^1$, $R^2$, $R^3$, R4, and $R^5$ represents (a) an aryl group such as a phenyl group, (b) a straight or branched alkyl group containing 1 to 12 carbon atoms, (c) a cyclic alkyl group containing 3 to 12 carbon atoms, (d) a straight or branched alkenyl group containing 2 to 12 carbon atoms, and (e) a cyclic alkenyl group containing 3 to 12 carbon atoms. Examples of the alkyl group are, specifically, a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopentyl group, and a cyclohexyl group. An Example of the alkenyl group is, specifically, an allyl group.

Note that, the hydrocarbon group may further include a functional group including an atom that is inert to the reaction and process (purification) of the present invention, for example, a fluorine atom, a nitrogen atom, an oxygen atom, a sulfur atom, that is, an inert functional group. Examples of the functional group are a methoxy group, a methylthio group, an N,N-dimethylamino group, an o-anis group, a p-anis group, a trimethylsilyloxy group, a dimethyl-t-butylsilyloxy group, and a trifluoromethyl group.

In the general formula, the alkoxy group for the substitutional group represented by $R^1$, $R^2$, $R^3$, $R^4$, and $R^5$ is represented by General Formula (A):

 (A)

(where Ra represents a hydrocarbon group).

In the general formula, the hydrocarbon represented by Ra specifically represents (a) an aryl group, (b) a straight or branched alkyl group containing 1 to 12 carbon atoms, (c) a cyclic alkyl group containing 3 to 12 carbon atoms, (d) straight or branched alkenyl group containing 2 to 12 carbon atoms, and (e) a cyclic alkenyl group containing 3 to 12 carbon atoms.

Examples of the alkoxy group represented by General Formula (A) are, specifically, a methoxy group, an ethoxy group, an n-propoxy group, an isopropoxy group, an n-butoxyl group, an isobutoxyl group, a sec-butoxy group, a t-butoxy group, a cyclohexyloxy group, an allyloxy group, and a phenoxy group.

Note that the tris(fluoroaryl)borane represented by the foregoing General Formula (1) is, for example, obtained by a method for reacting fluoroaryl magnesium halide and a borane compound.

Examples of the hydrocarbon solvent are (a) an aliphatic hydrocarbon solvent such as a saturated hydrocarbon solvent, an unsaturated hydrocarbon solvent, and an alicyclic hydrocarbon solvent and (b) an aromatic hydrocarbon solvent.

As the hydrocarbon solvent, the aliphatic hydrocarbon solvent is more preferable. Specifically, examples of the hydrocarbon solvent are 2,2-dimethylbutane, 2,3-dimethylbutane, 2,2,3-trimethylbutane, pentane, 2,2-dimethylpentane, 2,3-dimethylpentane, 2,4-dimethylpentane, 3,3-dimethylpentane, 2-methylpentane, 3-methylpentane, 2,2,4-trimethylpentane, 2,3,4-trimethylpentane, hexane, 2-methylhexane, 3-methylhexane, 2,2-dimehtylhexane, 2,4-dimethylhexane, 2,5-dimetylhexane, 3,4-dimehtylhexane, heptane, 2-methylheptane, 3-methylheptane, 4-methylheptane, 2,3-dimethylheptane, octane, nonane, decane, undecane, dodecane, tridecane, pentene, hexene, heptene, octene, cyclopentane, methylcyclopentane, ethylcyclopentane, cyclohexane, methylcyclohexane, 1,2-dimethylcyclohexane, 1,3-dimethylcyclohexane, 1,4-dimethylcyclohexane, ethylcyclohexane, cycloheptane, cyclooctane, cyclopentene, and cyclohexene. One of those hydrocarbon solvents may be used solely or more than two of those hydrocarbon solvents may be appropriately mixed and used. Moreover, commercial hydrocarbon solvents such as IsoparC, IsoparE, and IsoparG (any of them are Registered Trademarks) supplied from Exxon Corp. may be used.

It is preferable that the hydrocarbon solvent is substantially an aliphatic hydrocarbon solvent. For example, bis(pentafluorophenyl)borinic acid, which is a bis(fluoroaryl)borane derivative, is relatively soluble to the aromatic hydrocarbon solvent such as toluene. Thus, bis(pentafluorophenyl)borinic acid is obtained in a low yield when isolation of bis(pentafluorophenyl)borinic acid is carried out by filtration of a reaction mixture after concentration, in case the aromatic hydrocarbon solvent is used as a solvent. Because of this, it is necessary to have a step of concentrating to dryness the reaction mixture by distilling off the solvent, in order to have a high yield for isolation of the bis(pentafluorophenyl)borinic acid.

On the other hand, the bis(fluoroaryl)borane derivative has a low solubility for the aliphatic hydrocarbon solvent. Thus, in case the hydrocarbon solvent is substantially an aliphatic hydrocarbon solvent, it is possible to easily obtain the bis(fluoroaryl)borane derivative in a high yield by filtration of the bis(fluoroaryl)borane derivative after concentration of the reaction mixture.

Note that, in the present invention, the wording "the hydrocarbon solvent is substantially an aliphatic hydrocarbon solvent" means that a ratio of the aliphatic hydrocarbon solvent in the hydrocarbon solvent is within a range of 80% by weight to 100% by weight, and more preferably within a range of 95% by weight to 100% by weight.

The compound (2) used a starting raw material is a compound represented by General Formula (2):

 (2)

(where each of $R^0$, $R^6$, and $R^7$ independently represents one of a hydrogen atom and a hydrocarbon group, M represents an atom belonging to Group 15 or Group 16, and n represents 0 or 1).

In the general formula, the hydrocarbon for the substitutional groups represented by $R^0$, R6, and $R^7$, specifically represents (a) an aryl group such as a phenyl group, (b) a straight or branched alkyl group containing 1 to 12 carbon atoms, (c) a cyclic alkyl group containing 3 to 12 carbon atoms, (d) a straight or branched alkenyl group containing 2 to 12 carbon atoms, and (e) a straight or branched alkenyl group containing 3 to 12 carbon atoms. Examples of the alkyl group are specifically, a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopentyl group, and a cyclohexyl group. An Example of the alkenyl group is, specifically, an allyl group. Preferable as the substitutional group represented by $R^0$ are a hydrogen atom or a methyl group and an ethyl group among the alkyl groups listed above.

In the general formula, a nitrogen atom or an oxygen atom is more preferable among atoms belong to Group 5b (Group 15 in the long periodic table) or Group 6b (Group 16 in the long periodic table) for the substitutional group represented by M.

Examples of the compound (2) are, specifically, water, methanol, ethanol, ammonia, methylamine, dimethylamine, ethylamine, and diethylamine. Among those, it is more preferable to use water as the compound (2). In case, water is used as the compound (2), bis(fluoroaryl)borinic acid is produced by hydrolysis of tris(fluoroaryl)borane.

As described above, in the present method for manufacturing, it is a preferable embodiment in which water is used as the compound (2) so as to carry out the hydrolysis, so that the bis(fluoroaryl)borinic acid will be obtained. Further, it is more preferable that the bis(fluoroaryl)borinic acid is bis(pentafluorophenyl)borinic acid.

By reacting the tris(fluoroaryl)borane with the compound (2) in the hydrocarbon solvent, the bis(fluoroaryl)borane derivative is obtained in the reaction mixture in which the bis(fluoroaryl)borane derivative is dissolved or suspended in the hydrocarbon solvent, the bis(fluoroaryl)borane derivative being represented by General Formula (3):

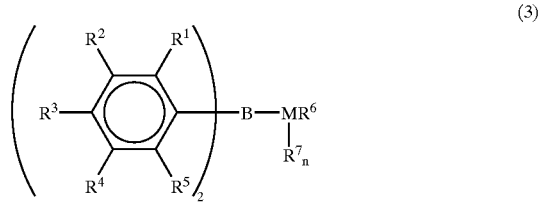

(3)

(where each of $R^1$, $R^2$, $R^3$, $R^4$, and $R^5$ independently represents one of a hydrogen atom, a fluorine atom, a hydrocarbon group, and an alkoxy group, at least one of $R^1$, $R^2$, $R^3$, $R^4$, and $R^5$ representing the fluorine atom, and each of $R^6$ and $R^7$ independently represents one of a hydrogen atom and a hydrocarbon group, M represents an atom belonging to Group 15 or Group 16, and n represents 0 or 1).

A method of mixing Tris(fluoroaryl)borane and the compound (2) in the hydrocarbon solvent may be for example, a method of dissolving the tris(fluoroaryl)borane in the hydrocarbon solvent so as to prepare a solution, then adding the compound (2) into the solution, a method of adding the tris(fluoroaryl)borane and the compound (2) to the hydrocarbon solvent at the same time and mixing it, or a method of adding tris(fluoroaryl)borane in the hydrocarbon solvent in which the compound (2) has been added, and mixing it.

Tris(fluoroaryl)borane and the compound (2) are mixed in the hydrocarbon solvent preferably at a temperature in a range of −100° C. to 300° C., and more preferably at a temperature in a range of 0° C. to 200° C.

By mixing the tris(fluoroaryl)borane and the compound (2) in the hydrocarbon solvent, a complex of the tris (fluoroaryl)borane and the compound (2) is formed. The bis(fluoroaryl)borane derivative is obtained by heating the solution, which contains the complex.

For example, in case where (a) tris(pentafluorophenyl) borane (($C_6F_5)_3B$), in which all of $R^1$, $R^2$, $R^3$, $R^4$, and $R^5$ in General Formula (1) are fluorine, and (b) water ($H_2O$) in which of $R^0$ and $R^6$ are hydrogen, M is oxygen and n=0, are used, a complex of the tris (pentafluorophenyl)borane and water is formed in the hydrocarbon solvent. Then, the complex of the tris (pentafluorophenyl)borane and water is heated thereby producing bis(pentafluorophenyl)borinic acid (($C_6F_5)_2BOH$).

While the bis(pentafluorophenyl)borinic acid, which is a bis(fluoroaryl)borane derivative, is useful as a polymerization catalyst, a polymerization co-catalyst, and a catalyst for photopolymerization of silicone, $(C_6F_5)B(OH)_2$, which is a byproduct of the reaction, reduces polymerization activity. Thus, it is preferable to suppress an amount of the byproduct as much as possible. Moreover, $(C_6F_5)B(OH)_2$ tends to be dehydrated so as to be condensed depending on the condition of purification, and may produce boroxine, which is a trimer. This boroxine is also not preferable as impurities. Thus, the amount of the boroxine produced need be suppressed as much as possible. Moreover, tris (pentafluorophenyl)borane, which is a raw material, is not preferable as impurities. Thus, it is necessary to have the conversion as high as possible.

For this reason, the reaction of the tris(fluoroaryl) borane and the compound (2) is carried out in the molar ratio ranging from 1:0.9 to 1:1.1 so that the conversion of the tris(fluoroaryl)borane will be high and the production of $(C_6F_5)B(OH)_2$, the byproduct of the reaction, will be suppressed, thereby obtaining $(C_6F_5)_2B(OH)$, the target compound with a high yield.

In the reaction of tris(fluoroaryl)borane and the compound (2) in the hydrocarbon solvent, it is more preferable that the hydrocarbon solvent is used in such an amount in which concentration of the tris(fluoroaryl) borane is within a range between 0.1% by weight and 80% by weight, and it is further preferable that the hydrocarbon solvent is used in such an amount in which concentration of the tris(fluoroaryl)borane is within a range between 1% by weight and 30% by weight.

It is more preferable that the reaction is carried out at a temperature in a range from 0° C. to 300° C., and it is further preferable that the reaction is carried out at a temperature in a range from 50° C. to 200° C. Reaction time may be appropriately set in accordance with combination of the tris(fluoroaryl)borane and the compound (2) and/or the temperature at which the reaction is carried out.

The bis(fluoroaryl)borane derivative, which is the target compound, is obtained by the reaction. The reaction mixture obtained by the reaction contains a fluorobenzyl compound, which is by-produced together with the bis (fluoroaryl) borane derivative. For example, in case tris (pentafluorophenyl)borane and water are used as the raw materials, pentafluorobenzen ($C_6F_5H$) is contained in the reaction mixture, together with bis(pentafluorophenyl) borinic acid, which is the target bis (fluoroaryl)borane derivative.

It is preferable that the reaction is carried out while the hydrocarbon solvent is distilled off. With the arrangement in which the reaction is carried out while the hydrocarbon solvent is distilled off, it is possible to easily remove the pentafluorobenzen, which is by-produced in the reaction.

The reaction mixture obtained by the reaction is concentrated, and if necessary the thus concentrated reaction mixture is cooled, so as to precipitate, from the reaction mixture, crystal of the bis(fluoroaryl)borane derivative, which is the target compound.

As to conditions for the concentration of the reaction mixture, it is more preferable that the reaction mixture is concentrated until concentration of a compound derived from tris(fluoroaryl)borane originally added in the solution reaches a range between 5% by weight and 100% by weight. It is further preferable that the reaction mixture is concentrated until the concentration of the compound derived from tris(fluoroaryl)borane originally added in the solution reaches a range between 10% by weight and 80% by weight. As to pressure during the concentration, there is no particular limitation. Thus, the pressure during the concentration may be ordinary pressure (atmospheric pressure) or reduced pressure.

It is more preferable that a temperature to which the reaction mixture is cooled down for precipitating the crystal, is within a range from −50° C. to 50° C. It is further preferable that the temperature to which the reaction mixture is cooled down for precipitating the crystal, is within a range from −20° C. to 30° C. Duration for concentrating the reaction mixture and duration for cooling the reaction mixture may be appropriately set in accordance with an amount of the reaction mixture or the like condition. By filtering out the crystal thus precipitated, it is possible to easily isolate bis(fluoroaryl)borane derivative from the reaction mixture.

It is preferable that the thus obtained bis(fluoroaryl) borane derivative has purity of 98% or more. For example, bis(pentafluorophenyl)borinic acid having a high purity is useful as a polymerization catalyst, a polymerization co-catalyst, and a photopolymerization catalyst for silicone, because the bis(pentafluorophenyl)borinic acid having a high purity has not a large amount of impurities, which reduces polymerization activity.

It is possible to easily isolate the bis(fluoroaryl) borane derivative by concentrating, cooling, and filtering the reaction mixture as described above. Moreover, a cake obtained by filtering the reaction mixture is washed with a poor solvent, if necessary. In this way, it is possible to remove the byproduct and the like from the cake. By doing this, it is possible to isolate and purify the bis(fluoroaryl) borane derivative with ease and at a low cost.

BEST MODE FOR CARRYING OUT THE INVENTION

The present invention is explained in more detail below referring to examples and comparative examples. However, the present invention is not limited to those. Note that NMR (Nuclear Magnetic Resonance) spectrum data was measured in the examples in such a manner that tetramethyl silane (TMS) was a standard substance for $^1$H-NMR spectrum data, while trifluoro acetic acid was a standard substance for $^{19}$F-NMR spectrum data so that signals of the standard substances were assumed to be 0 ppm.

EXAMPLE 1

686.78 g of IsoparE (supplied from Exxon Corp.) solution containing 18.886 g of tris(pentafluorophenyl)borane as tris (fluoroaryl)borane and 0.671 g of water (1.0 molar equivalent vs. tris (pentafluorophenyl borane) as a compound expressed by the general formula (2) were added into a reaction vessel equipped with a reflux condenser, a thermometer, a dropping funnel and a stirrer.

Next, the content of the reaction vessel was heated to 100° C. with stirring. Reaction was carried out for 4 hours at 100° C. A part of the reaction mixture obtained from the reaction for 4 hours was analyzed by $^{19}$F-NMR. It showed that conversion of tris (pentafluorophenyl)borane was 100%, while a yield of bis(pentafluorophenyl)borinic acid was 99.0% and a yield of pentafluorophenylboronic acid was 1.0%.

EXAMPLE 2

The reaction mixture obtained in Example 1 was added in a reaction vessel equipped with a distillation apparatus, a thermometer, a dropping funnel, and a stirrer, and concentrated under reduced pressure, namely, at 8.67 kPa (65 mmHg). The concentration under reduced pressure distilled out distillate of 605.88 g.

The concentrated solution (residues) obtained by the concentration under reduced pressure was cooled down to 13° C. The precipitate obtained by the cooling of the concentrated solution was filtered to give a cake (solid deposited on a filter medium). The cake was washed with 20 ml of hexane. The thus obtained cake was dried under reduced pressure. The dried cake had a weight of 11.116 g. The cake was analyzed by $^{19}$F-NMR. It showed that the cake contained bis(pentafluorophenyl)borinic acid of 98.6% by weight, which is a bis(fluoroaryl)borane derivative, and pentafluorophenylboronic acid of 1.4% by weight. NMR spectrum data of the bis(pentafluorophenyl)borinic acid in the cake was:

19F-NMR (benzene-d6, δ);−57.6, −72.7, −85.6 ppm.

Comparative Example 1

682.42 g of IsoparE (supplied from Exxon Corp.) solution containing 18.767 g of tris(pentafluorophenyl)borane and 1.980 g of water (3.0 molar equivalent vs. the tris (pentafluorophenyl)borane) were added to a reaction vessel equipped with a reflux condenser, a thermometer, a dropping funnel and a stirrer.

Next, the content of the reaction vessel was heated up to 100° C. with stirring. Reaction was carried out for 4 hours at 100° C. A part of the reaction mixture obtained from the reaction for 4 hours was analyzed by $^{19}$F-NMR. It showed that the conversion of tris(pentafluorophenyl)borane was 64%, while a yield of bis(pentafluorophenyl)borinic acid was 41% and a yield of pentafluorophenylboronic acid was 23%. The reaction was continued for another one hour at 100° C. A part of the reaction mixture was analyzed by $^{19}$F-NMR. It showed that the conversion of tris (pentafluorophenyl)borane was 75%, while the yield of bis(pentafluorophenyl)borinic acid was 37% and the yield of pentafluorophenylboronic acid was 38%. Thus, it was observed that the yield of bis(pentafluorophenyl)borinic acid was reduced.

Comparative Example 2

701.34 g of IsoparE (supplied from Exxon Corp.) solution containing 19.287 g of tris(pentafluorophenyl)borane, and 1.251 g of water (1.8 molar equivalent vs. the tris (pentafluorophenyl) borane) were added into a reaction vessel equipped with a reflux condenser, a thermometer, a dropping funnel and a stirrer.

Next, the content of the reaction vessel was heated up to 100° C. with stirring. Reaction was carried out for 4 hours at 100° C. A part of the reaction mixture obtained from the reaction for 4 hours was analyzed by $^{19}$F-NMR. It showed that the conversion of tris(pentafluorophenyl)borane was 87%, while a yield of bis(pentafluorophenyl)borinic acid was 83% and a yield of pentafluorophenylboronic acid was 4%. The reaction was continued for another two hours at 100° C. A part of the reaction mixture was analyzed by $^{19}$F-NMR. It showed that the conversion of tris (pentafluorophenyl)borane was 96%, while the yield of bis(pentafluorophenyl)borinic acid was 89% and the yield of pentafluorophenylboronic acid was 7%.

A method of the present invention for producing a bis (fluoroaryl)borane derivative is so characterized that the hydrocarbon solvent is substantially an aliphatic hydrocarbon solvent.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

Industrial Applicability

A method for producing a bis(fluoroaryl)borane derivative, as described above, is so arranged that tris (fluoroaryl)borane and a compound are reacted in a hydrocarbon solvent, in a molar ratio ranging from 1:0.9 to 1:1.1, the compound being represented by General Formula (2).

Specifically, with an arrangement in which the reaction is carried out in the molar ratio within the range, it is possible to suppress production of a byproduct while the bis (fluoroaryl)borane derivative is produced. In this way, it is possible to obtain the bis(fluoroaryl)borane derivative with a high purity.

A method of the present invention for producing a bis (fluoroaryl)borane derivative, as described above, is so arranged that tris(fluoroaryl)borane and a compound are mixed in a hydrocarbon solvent, in a molar ratio ranging from 1:0.9 to 1:1.1, and the tris(fluoroaryl)borane and the compound are reacted in a hydrocarbon solvent, while the hydrocarbon solvent is distilled off, the compound being represented by General Formula (2).

For example, as to reaction of tris(pentafluorophenyl) borane(($C_6F_5$)$_3$B) with water, $C_6F_5H$ is produced as a byproduct during the reaction. However, with an arrangement in which the reaction is carried out while the hydrocarbon solvent is distilled off, it is possible to easily remove the $C_6F_5H$ from the reaction mixture. In short, it is possible to easily remove the byproduct of the reaction with the arrangement the reaction is carried out while the hydrocarbon solvent is distilled off.

By doing this, it is possible to obtain the bis (fluoroaryl) borane derivative with a high purity.

As described above, the method of the present invention for producing the bis(fluoroaryl)borane derivative is so arranged that the hydrocarbon solvent is substantially an aliphatic hydrocarbon solvent.

Therefore, it is possible to easily separate, from the reaction mixture, the bis(fluoroaryl)borane derivative, such as the bis(pentafluorophenyl)borinic acid, by concentrating and filtering the reaction mixture.

With this arrangement, it is possible to produce the bis(fluoroaryl)borane derivative with ease and at a low cost, while it is possible to easily isolate and purify the bis (fluoroaryl)borane derivative with ease and at a low cost.

What is claimed is:

1. A method for producing a bis(fluoroaryl)borane derivative represented by Formula (3):

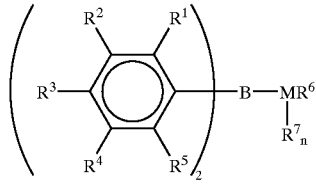

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, M represents an atom belonging to Group 15 or Group 16, and n represents 0 or 1, the method comprising the step of:
reacting tris(fluoroaryl)borane and a compound in a hydrocarbon solvent, in a molar ratio ranging from 1:0.9 to 1:1.1, wherein
the tris(fluoroaryl)borane is represented by Formula (1):

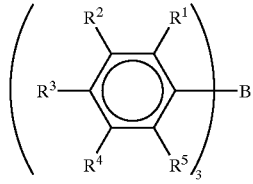

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and the compound is represented by Formula (2):

where each of $R^0$, $R^6$, and $R^7$ independently represents one of a hydrogen atom and a hydrocarbon group, M represents an atom belonging to Group 15 or Group 16, and n represents 0 or 1.

2. The method for producing the bis(fluoroaryl)borane derivative as set forth in claim 1, wherein the hydrocarbon solvent is substantially an aliphatic hydrocarbon solvent.

3. The method for producing the bis(fluoroaryl)borane derivative as set forth in claim 1, wherein the hydrocarbon solvent is used in such an amount in which concentration of the tris(fluoroaryl)borane is within a range between 0.1% by weight and 80% by weight.

4. The method for producing the bis(fluoroaryl)borane derivative as set forth in claim 1, wherein:
the tris(fluoroaryl)borane and the compound represented by Formula (2) are reacted in the hydrocarbon solvent at a temperature within a range between 0° C. and 300° C.

5. The method for producing the bis(fluoroaryl)borane derivative as set forth in claim 1, wherein the bis(fluoroaryl) borane derivative is bis(pentafluorophenyl)borinic acid.

6. The method for producing the bis(fluoroaryl)borane derivative as set froth in claim 1, wherein the bis(fluoroaryl) borane derivative has a purity of 98% or more.

7. A method for producing a bis(fluoroaryl)borane derivative represented by Formula (3):

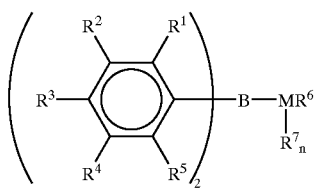

(3)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, and each of $R^6$ and $R^7$ independently represents one of a hydrogen atom and a hydrocarbon group, M represents an atom belonging to Group 15 or Group 16, and n represents 0 or 1, the method comprising the steps of:

(a) mixing tris(fluoroaryl)borane and a compound in a hydrocarbon solvent, in a molar ratio ranging from 1:0.9 to 1:1.1; and (b) reacting the tris(fluoroaryl)borane and the compound in a hydrocarbon solvent, while the hydrocarbon solvent is distilled off, wherein the tris(fluoroaryl)borane being represented by Formula (1):

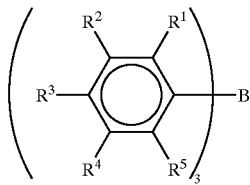

(1)

where each of $R^1$, $R^2$, $R^3$, $R^4$, and $R^5$ independently represents one of a hydrogen atom, a fluorine atom, a hydrocarbon group, and an alkoxy group, provided at least one of $R^1$, $R^2$, $R^3$, $R^4$, and $R^5$ is a fluorine atom, the compound being represented by Formula (2):

$$R^0\text{—}MR^6(R^7)_n \qquad (2)$$

where each of $R^0$, $R^6$, and $R^7$ independently represents one of a hydrogen atom and a hydrocarbon group, M represents an atom belonging to Group 15 or Group 16, and n represents 0 or 1.

8. The method for producing the bis(fluoroaryl)borane derivative as set forth in claim 7, wherein:

the tris(fluoroaryl)borane and the compound represented by Formula (2) are mixed in the hydrocarbon solvent at a temperature within a range between −100° C. and 300° C.

9. The method for producing the bis(fluoroaryl)borane derivative as set forth in claim 7, wherein:

reacting step (b) is carried out while the hydrocarbon solvent is distilled off so that concentration of the bis(fluoroaryl)borane derivative in the reaction mixture reaches a range between 5% by weight and 100% by weight in terms of the tris(fluoroaryl)borane, the reaction mixture obtained by reacting, in the hydrocarbon solvent, the tris(fluoroaryl) borane and the compound represented by Formula (2).

* * * * *